(12) United States Patent
Huang (10) Patent No.: US 7,187,816 B2
(45) Date of Patent: Mar. 6, 2007

(54) IN-FIBER WHITELIGHT INTERFEROMETRY USING LONG-PERIOD FIBER GRATING

(75) Inventor: Haiying Huang, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 11/301,565

(22) Filed: Dec. 12, 2005

(65) Prior Publication Data

US 2006/0126991 A1    Jun. 15, 2006

Related U.S. Application Data

(60) Provisional application No. 60/635,628, filed on Dec. 13, 2004.

(51) Int. Cl.
  *G02B 6/00* (2006.01)
  *G02B 6/34* (2006.01)
(52) U.S. Cl. ............................ 385/12; 385/37
(58) Field of Classification Search ...................... None
  See application file for complete search history.

(56) References Cited

U.S. PATENT DOCUMENTS

| 4,293,188 | A | 10/1981 | McMahon |
|---|---|---|---|
| 4,596,925 | A | 6/1986 | Gilby |
| 5,301,001 | A | 4/1994 | Murphy et al. |
| 5,420,688 | A | 5/1995 | Farah |
| 5,641,956 | A | 6/1997 | Vengsarkar et al. |
| 5,864,641 | A | 1/1999 | Murphy et al. |
| 5,891,747 | A | 4/1999 | Farah |
| 5,945,666 | A | 8/1999 | Kersey et al. |
| 5,969,342 | A | 10/1999 | Feng et al. |
| 6,021,240 | A | 2/2000 | Murphy et al. |
| 6,035,082 | A | 3/2000 | Murphy et al. |
| 6,058,226 | A | 5/2000 | Starodubov |
| 6,075,907 | A | 6/2000 | Krol |
| 6,317,538 | B1 | 11/2001 | Shigehara et al. |
| 6,330,105 | B1 | 12/2001 | Rozelle et al. |
| 6,343,168 | B1 | 1/2002 | Murphy et al. |
| 6,366,722 | B1 | 4/2002 | Murphy et al. |
| 6,542,668 | B2 | 4/2003 | Gaylord et al. |
| 6,833,541 | B2 | 12/2004 | Shu et al. |
| 6,898,337 | B2 * | 5/2005 | Averett et al. ................ 385/12 |
| 2003/0141440 | A1 | 7/2003 | Kim et al. |
| 2003/0209655 | A1 | 11/2003 | Wang |
| 2004/0022475 | A1 * | 2/2004 | Pennington ................. 385/12 |
| 2004/0114849 | A1 | 6/2004 | Shah et al. |
| 2004/0115824 | A1 | 6/2004 | Ponce et al. |
| 2004/0218847 | A1 | 11/2004 | Averett et al. |
| 2004/0245444 | A1 | 12/2004 | MacDougall |
| 2005/0002606 | A1 | 1/2005 | James et al. |

OTHER PUBLICATIONS

Dabbs et al., "Fiber-optic confocal microscope: FOCON", Applied Optics, Jun. 1, 1992, vol. 31, No. 16, pp. 3030-3035.

(Continued)

*Primary Examiner*—Sung Pak
*Assistant Examiner*—Tina M. Wong
(74) *Attorney, Agent, or Firm*—Baker & Daniels LLP (57) ABSTRACT

An optical fiber sensor is provided for displacement measurement, pressure measurement, refractive index measurement, bio/chemical detection, and/or microscopy.

27 Claims, 10 Drawing Sheets

OTHER PUBLICATIONS

P.G. Davis and I.J. Bush et al. "Fiber Optic Displacement Sensor", Reprint: Fourth Pacific Northwest Fiber Workshop, May 6, 1998 SPIE.

Jasapara et al., "Accurate noncontact optical fiber diameter measurement with spectral interferometry", Optics Letters, Apr. 15, 2003, vol. 28, No. 8, pp. 601-603.

Juskaitis et al., "Direct-view fiber-optic confocal microscope", Optics Letters, Nov. 16, 1994, vol. 19, No. 22, pp. 1906-1908.

MacPherson, et al. "Blast-pressure measurement with a high-bandwidth fibre optic pressure sensor", Meas. Sci. Technol. 11 (2000) 95-102.

Ruan, et al. "A precision Fiber Optic Displacement Sensor Based on Reciprocal Inteferometry", Optics Communications, 176, 2000, 105-112.

Swart, "Long-period grating Michelson refractometric sensor", Meas. Sci. Technol. 15 (2004), pp. 1576-1580.

Totsu, et al. "Ultra-miniature fiber-optic pressure sensor using white light interferometry", J. Micromech. Microeng. 15, (2005), 71-75.

Yang et al., "Surface profilometry with a fibre optical confocal scanning microscope", Meas. Sci. Technol. 11 (2000), pp. 1786-1791.

* cited by examiner

FIG.14A (A) DISTANCE

FIG.14B (B) PHASE SHIFT

IN-FIBER WHITELIGHT INTERFEROMETRY USING LONG-PERIOD FIBER GRATING

BACKGROUND AND SUMMARY OF THE INVENTION

This application claims the benefit of U.S. Provisional Application Ser. No. 60/635,628, filed Dec. 13, 2004, which is expressly incorporated by reference herein.

The present invention relates to an in-fiber whitelight interferometer (WLI) based on Long Period Fiber Grating (LPFG). More particularly, the present invention relates to optical fiber sensors for distance/displacement measurement, near-field surface profiling, vibration measurement, temperature measurement, pressure measurement, refractive index measurement, and bio/chemical detection.

Optical fiber sensors have been widely exploited for confocal microscopy, displacement measurement, temperature sensing, moisture monitoring, and bio/chemical detection, due to their compact size, ultra-fast response, and immunity to electromagnetic interference. The illustrated embodiment provides an in-fiber Michelson interferometric sensor based on the coupling effect of an LPFG. The two optical arms of the interferometer are the light waves propagating along a cladding region and a core region of a single mode fiber. The wave that propagates along the fiber core exits the fiber core, travels in a free space, reflects back from an object, and re-enters the fiber core. The wave that travels in the fiber cladding reflects back at a mirror end of the fiber and interferes with the core wave at a LPFG, thus generating a wavelength-modulated reflectance spectrum, from which the phase delay between these two optical waves can be calculated. Because the phase delay is measured by wavelength shift instead of intensity variation, the illustrated LPFG-based whitelight interferometer is more robust and less noise sensitive.

Distance variation and refractive index change of the free space can alter the phase delay between that wave travels along the fiber cladding and the wave that travels in the fiber core. As a result, the concept of the LPFG-based whitelight interferometry can be applied for distance/displacement measurement, near-field surface profile, vibration measurement, temperature measurement, pressure measurement, refractive index measurement, and bio/chemical detection.

Additional features of the invention will become apparent to those skilled in the art upon consideration of the following detailed description of the presently perceived best mode of carrying out the invention.

BRIEF DESCRIPTION OF THE DRAWINGS

The detailed description particularly refers to the accompanying figures in which.

DETAILED DESCRIPTION OF DRAWINGS

The complete disclosures of the following listed references are expressly incorporated herein by reference:

1. SWART, "Long-period grating Michelson refractometric sensor", Meas. Sci. Technol. 15 (2004), pgs. 1576–80
2. JASAPARA et al., "Accurate noncontact optical fiber diameter measurement with spectral interferometry", Optics Letters, Apr. 15, 2003, Vol. 28, No. 8, pgs. 601–603
3. DABBS et al., "Fiber-optic confocal microscope: FOCON", Applied 20 Optics, Jun. 6, 1992, Vol. 31, No. 16, pgs. 3030–35
4. JUSKAITIS et al., "Direct-view fiber-optic confocal microscope", Optics Letters, Nov. 16, 1994, Vol. 19, No. 22, pgs. 1906–08
5. YANG et al., "Surface profilometry with a fibre optical confocal scanning microscope", Meas. Sci. Technol. 11 (2000), pgs. 1786–91.
6. P. G. DAVIS and I. J. BUSH et al. "Fiber Optic Displacement Sensor", Reprint: Fourth Pacific Northwest Fiber Workshop, May 6, 1998 SPIE
7. RUAN, et al. "A precision Fiber Optic Displacement Sensor Based on Reciprocal Inteferometry", Optics Communications, 176, 2000, 105–112
8. TOTSU, et al. "Ultra-miniature fiber-optic pressure sensor using white 30 light interferometry", J. Micromech. Microeng. 15, (2005), 71–75
9. MACPHERSON, et al. "Blast-pressure measurement with a high-bandwidth fibre optic pressure sensor", Meas. Sci. Technol. 11 (2000) 95–102

Figure 1:
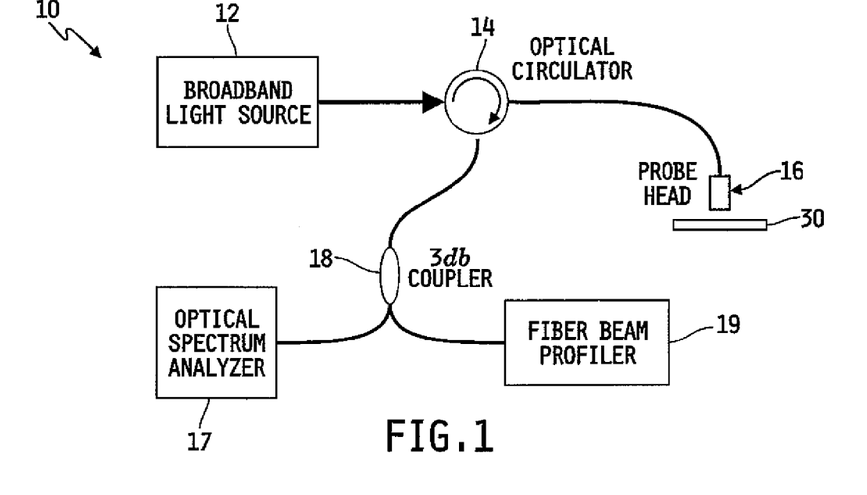
FIG. 1 is a block diagram of the optical fiber sensor of the present invention.
Figure 2A:
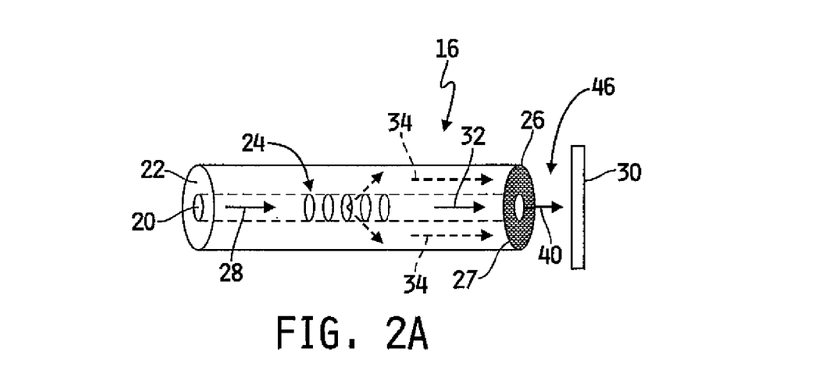
FIGS. 2A and 2B are diagrammatical views illustrating the optical path in the optical fiber sensor probe.
Figure 2B:
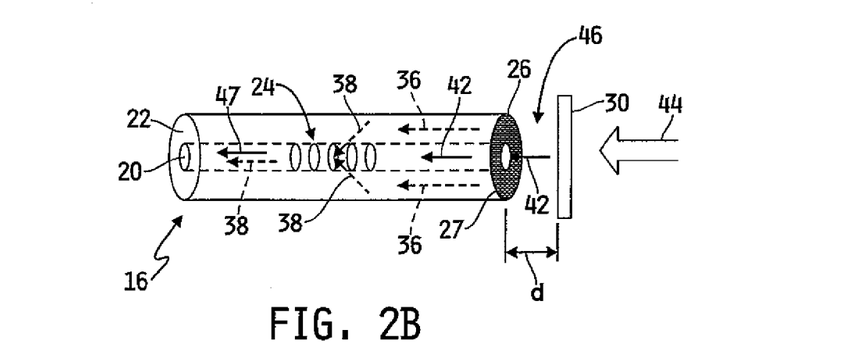

Referring now to the drawings, FIGS. 1, 2A and 2B illustrate an optical fiber sensor 10 that has nanometer axial distant resolution and can be used as a distance/displacement sensor, near-field surface profiler, vibration sensor, temperature sensor, pressure sensor, refractive index measurement sensor, and bio/chemical sensor. The illustrative embodiment will be discussed in terms of a displacement sensor.

The displacement sensor 10 of the present invention is based on the characteristics of a long period fiber grating, which couples optical wave from core mode to cladding mode. The measurement system illustratively includes a broadband light source 12, an optical circulator 14, a sensing probe 16, and an Optical Spectrum Analyzer (OSA) or a similar device 17, an optical coupler 18, and a fiber beam profiler 19 as shown in FIG. 1.

The probe 16 is illustratively a single mode fiber having an inner core 20, an outer cladding 22, and a long period fiber grating (LPFG) 24 embedded at selected distances from the cleaved fiber distal end 26. Fiber end 26 is coated with a mirror 27 over its cladding region 22 as shown in FIGS. 2A and 2B. A whitelight wave generated from the broadband light source 12 propagates along the optical fiber core 20 as illustrated by arrow 28 in FIG. 2A and is routed towards the LPFG 24 by the optical circulator 14. Upon encounter of the LPFG 24, part of the wave 28 continues to travel along the core 20 of the fiber toward a test sample 30 as indicated by the solid arrow 32 in FIG. 2A. Part of the wave gets coupled into the cladding area 22 as illustrated by arrow 34 in FIG. 2A. Wave 34 continues propagating along the cladding 22 toward end 26 until it reaches the mirror 27 on end 26 of the fiber. Reflecting from the mirror 27, this cladding-mode wave 34 retraces its path back toward the LPFG 24 as illustrated by dashed lines 36 in FIG. 2B.

At the LPFG 24, part of the reflective wave 34 is coupled back to core mode as illustrated by dashed lines 38. The part of wave 32 moving through core 20 exits the end 26 of probe 16 as illustrated by arrow 40 in FIG. 2A. Wave 40 strikes a sample 30 and is reflected back toward core as illustrated by arrows 42 in FIG. 2B. Therefore, the sensor illustrated in FIGS. 2A and 2B is adapted to measure the free space 46 between end 26 of probe 16 and the sample under test 30.

When the sample 30 is displaced in FIG. 2B the sensor 10 measures the change in free space 46 distance between the end 26 of probe 16 and the sample 30 as discussed below. When core-mode wave 42 encounters LPFG 24, part of the wave 42 reflected from the sample 30 stays in core 20 (illustrated by arrow 47) and thus interferes with the portion of wave 38 in core 20 which is reflected from the mirror 27. The phase delay between these two waves 47, 38 is caused by the difference between the refractive index of the cladding 22 and the fiber core 20, and from the air gap 46 illustrated by distance (d) between the end 26 sensor head 16 and the sample surface 30.

The transmission spectrum of the exiting wave front is modulated with multiple peaks since this phase delay is wavelength sensitive. With a fixed distance between the LPFG 24 and the fiber end 26, the number of peaks and the positions of these peaks are directly related to the distance between the fiber end 26 and the sample surface 30. Variation of this distance can thus be measured accurately by detecting small wavelength shifts in the spectrum using a suitable device such as an OSA 18. Calculations indicate that sub-nanometer resolution is achieved for an OSA 18 with 10 pm wavelength resolution. The LPFG-based displacement sensor of the illustrated embodiment measures the phase delay by wavelength shifts instead of intensity modulation and thus is more precise and noise-immune.

Illustrative Sensor Fabrication Process

Figure 7A:
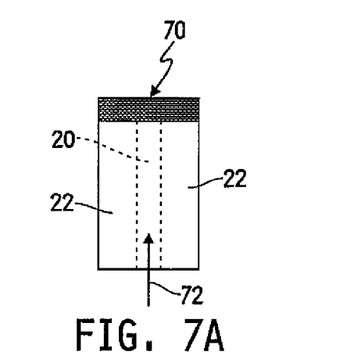
FIGS. 7A–7D illustrate an example optical fiber sensor fabrication procedure.
Figure 7B:
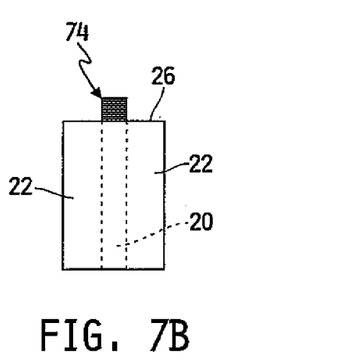
Figure 7C:
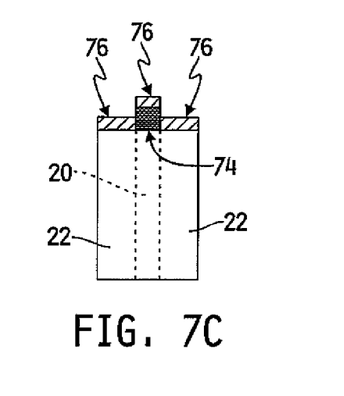
Figure 7D:
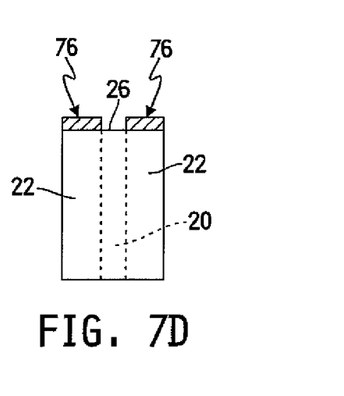

The sensor probe 16, as shown in FIGS. 2A and 2B, is illustratively fabricated from a single mode fiber (SMF). As illustrated, a Gold or Aluminum metallic thin film 76 is deposited on the cladding area 24 of the fiber cross-section and serves as a mirror to reflect light traveling in the cladding area 24. In an illustrative embodiment, a diameter of the core area is about 10 Am and a diameter of the cladding area is about 125 µm. The sensor 16 is illustratively fabricated using conventional semiconductor fabrication process. As shown in FIG. 7A, a negative photoresist layer 70 is first deposited on the fiber end 26. UV light from a UV LED or UV laser, for example, is then coupled into the fiber from the other end as illustrated by arrow 72. The UV light travels through the fiber along the fiber core 20 and exposes only the portion of the photoresist layer 70 covering the core 20. After development, a photomask 74 is created on top of the core area as illustrated in FIG. 7B. A metal layer 76 is then deposited on the cladding area 22 of the fiber as shown in FIG. 7C. Finally, the photomask 74 is etched away and the fiber core 20 is exposed as shown in FIG. 7D.

Illustrative Data Demodulation Process (Example One):

In one illustrated example, if the distance between the sensor end 26, 62 and the sample 30 (or membrane 56) is d, the optical path difference between the two waves (cladding mode and core mode) is:

$$2\Delta n \ast Lcav + 2n_m \ast d$$

Where $\Delta n = n_{clad} - n_{core}$ is the difference between refractive indices of the fiber core and fiber cladding and $n_m$ is the refractive index of the medium in the free space (for air, $n_m = 1$)

The reflectance as a function of wavelength λ is:

$$R(\lambda) = 1 - 4T_{co}(\lambda)T_{cl}(\lambda)\sin^2[2\ast\pi\ast(\Delta n \ast L_{cav} + n_m d)/\lambda + \theta]$$

Figure 4:
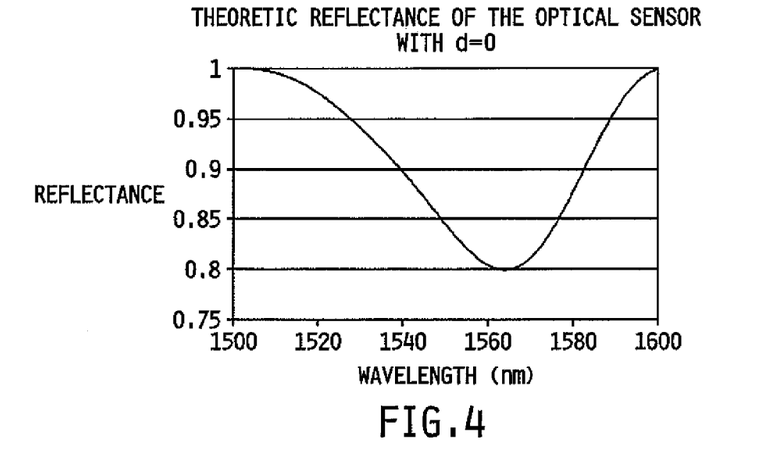
FIG. 4 is a theoretical reflectance spectrum.
Figure 5:
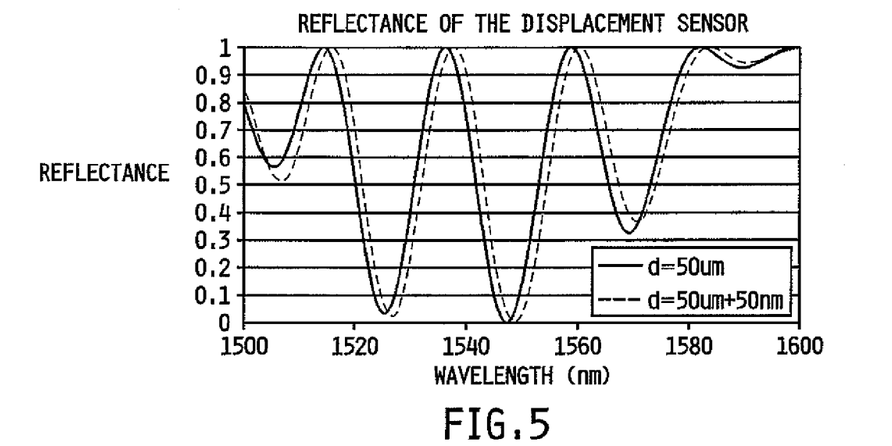
FIG. 5 is an illustrative shifted reflectance spectrum as a distance to a displacement of a test sample changes.
Figure 6:
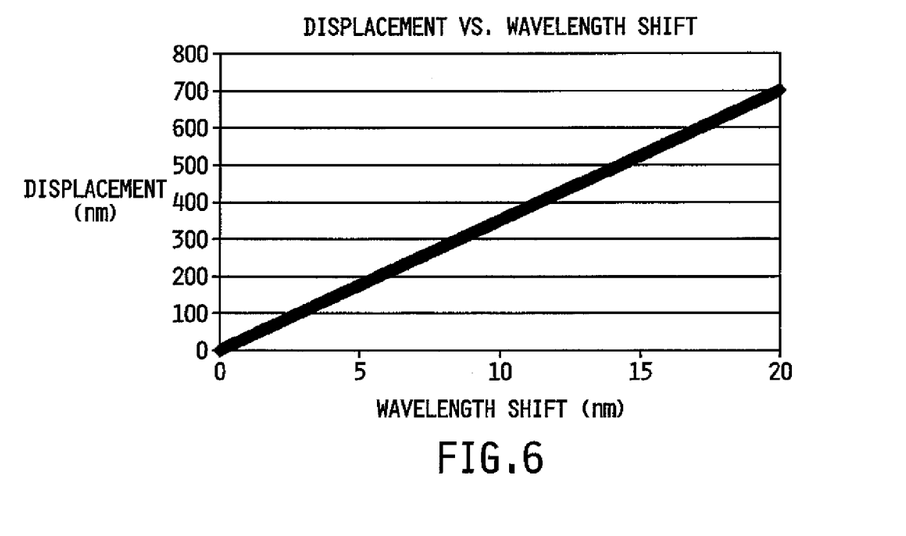
FIG. 6 shows the linear relationship between the displacement of the sample and the wavelength shift of the reflectance spectrum.

The shape of the reflectance spectrum is directly related to the distance between the sensor end 26, 62 and the testing sample 30, 56. The absolute distance between the sensor and the testing sample can thus be measured from the reflectance spectrum. For an optical fiber sensor with Δn=0.003, grating length L=12.5 mm, grating period=500 µm, cavity length Lcav=1 mm, the reflectance spectrum is as shown in FIG. 4 when the distance between the sensor and the testing surface is zero. As the distance increase, the number of dips in the reflectance spectrum increases. It can be seen from FIG. 5 that the reflectance spectrum is shifted to the right side as distance between the sensor and the sample increased by 50 µm from 50 µm to 50.05 um. The displacement of the sample can thus be measured from the wavelength shift. FIG. 6 shows the linear relationship between the displacement of the sample and the wavelength shift of the reflectance spectrum. In this case, the displacement resolution is illustratively 0.4 nm for a spectrum analyzer with 10 pm resolution.

In an illustrated example, the following source code is used. Illustratively, this code may be executed on a Compaq Presario CL1701 with Windows 2000 operation system, or other suitable hardware. The code is written in METLAB language.

```
================================= LPG.m
=====================================
% long period grating spectra calculation
clear; clc;
lamda0=1540e-9; % central wavelength
lamda=[1480:0.001:1600]*1e-9;
dn=0.003; % refractive index difference
nm=1.0; % refractive index of medium
```

-continued

```
D=500e-6;      %grating period
L=12.5e-3;     % grating length
k=pi/(4*L);    % coupling coefficient
Lcav=1e-3;     % cavity length
delta=pi/D*(lamda-lamda0)./lamda;   % eq. (5)
gamma=sqrt(k*k+delta.*delta);       % eq. (6)
Tco=cos(gamma*L).^2+delta.^2./gamma.^2.*sin(gamma*L).^2;    % eq. (3)
Tclad=k^2*sin(gamma*L).^2./gamma.^2;        % eq.(4)
dl0=50e-6+131e-9; % distance between sensor and surface
theta=0;       % phase shift
R=1-4*Tco.*Tclad.*sin(2*pi*(dn*Lcav+nm*dl0)./lamda+theta).^2;    % eq. (2) with additional distance d
index_o=find(R==min(R));     % find the deepest dip
lamda_o=lamda(index_o);      % find the wavelength at the dip
plot((lamda-lamda0)*1e9, R);   % plot reflectance spectrum
xlabel('wavelength (nm)'); ylabel('Reflectance'); title('Reflectance Spectrum at Original Distance');
hold on;
plot((lamda_o-lamda0)*1e9,R(index_o), '*');    % plot the tip of the dip
  for ii=1:1500     % loop with increasing distance
    dl(ii)=dl0+ii*0.4e-9; % change of distance between sensor and surface
      R1=1-4*Tco.*Tclad.*sin(2*pi*(dn*Lcav+nm*dl(ii))./lamda+theta).^2;     % reflectance
    index=find(R1==min(R1));     % find the deepest dip
    lamda_m=lamda(index);      % find the wavelength at the dip
    d_lamda(ii)=(lamda_m-lamda_o)*1e9;   % wavelength shift between the original spectrum and current spectrum
end
 figure;
plot(d_lamda, (dl-dl0)*1e9); % plot the wavelength shift vs. distance d
xlabel('wavelength shift (nm)'); ylabel('distance (nm)');
title('relationship between wavelength shift and distance variation');
```

Figure 8:
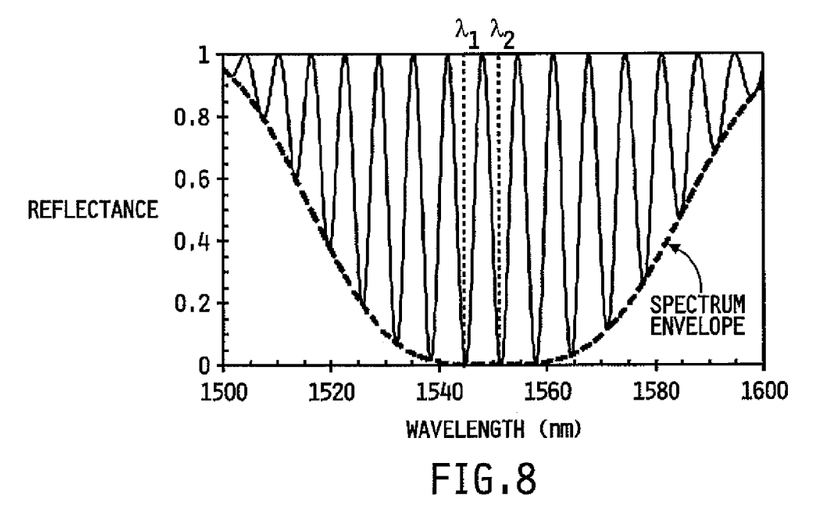
FIG. 8 is an illustrative fringe spectrum of the LPFG-based interferomic distance sensor.

Illustrative Data Demodulation Process (Example Two):

In another example of the data demodulation process, the Optical Path Difference (OPD) between the core mode and the cladding mode is composed of the difference between the refractive index of the cladding and the fiber core, and the cavity distance between the sensor head and the sample surface. An illustrative equation is as follows:

$$OPD = 2\Delta nL + 2n_m d_0 \quad \text{Equation (1):}$$

Where $\Delta n = n_{clad} - n_{core}$ is the difference between the refractive index (n) of the core and the cladding, L is the distance between the center of the LPFG and the fiber end, $n_m$ is the refractive index of the medium in the free space (for air, $n_m=1$), and $d_o$ is the cavity distance between the fiber end and the sample. Based on the theory of mode coupling in LPFG, the reflectance R as a function of wavelength $\lambda$ is:

Equation (2):

$$R(\lambda) = [1 - 2T_{co}(\lambda)T_{cl}(\lambda)] + 2T_{co}(\lambda)T_{cl}(\lambda)\cos\left[\frac{4\pi(\Delta nL_{cav} + n_m d_0)}{\lambda} + \theta_0\right]$$

Where $T_{co}(\lambda)$ is the transmittance of the LPFG, $T_{cl}(\lambda)$ is the transmittance from the fiber core to the cladding, and $\theta_0$ is the phase shift, which is usually unknown. FIG. 8 illustrates a typical fringe spectrum of a LPFG-based distance sensor, which is a combined effect of the LPFG transmittance and the relative phase delay between the waves in the two optical paths. The fringe envelope is controlled by the parameters of the LPFG. The spacing and the positions of the peaks and valleys, i.e. the fringes, in the spectrum are directly related to the OPD between the core mode and the cladding mode. The cavity length d is related to the positions of two adjacent fringes, $\lambda_1$ and $\lambda_2$, as:

Equation (3):

$$d = \frac{\lambda_1 \lambda_2}{2n_0(\lambda_2 - \lambda_1)} - \Delta nL$$

This removes the ambiguity in distance measurement. However, this method can not achieve high resolution due to quantization errors. Therefore, the illustrated embodiment uses a data interrogation technique to extract the absolute distance $d_0$ and the phase shift $\theta_0$. This illustrative data interrogation technique includes two steps: 1) obtain a rough estimation of the absolute distance $d_0$ and the phase shift $\theta_0$ by matching two fringes in the estimated fringe spectrum with two fringes in the measurement fringe spectrum; and 2) calculate the distance $d_0$ and the phase shift $\theta_0$ more precisely from the difference between the measured fringe spectrum and the estimated fringe spectrum.

Figure 9:
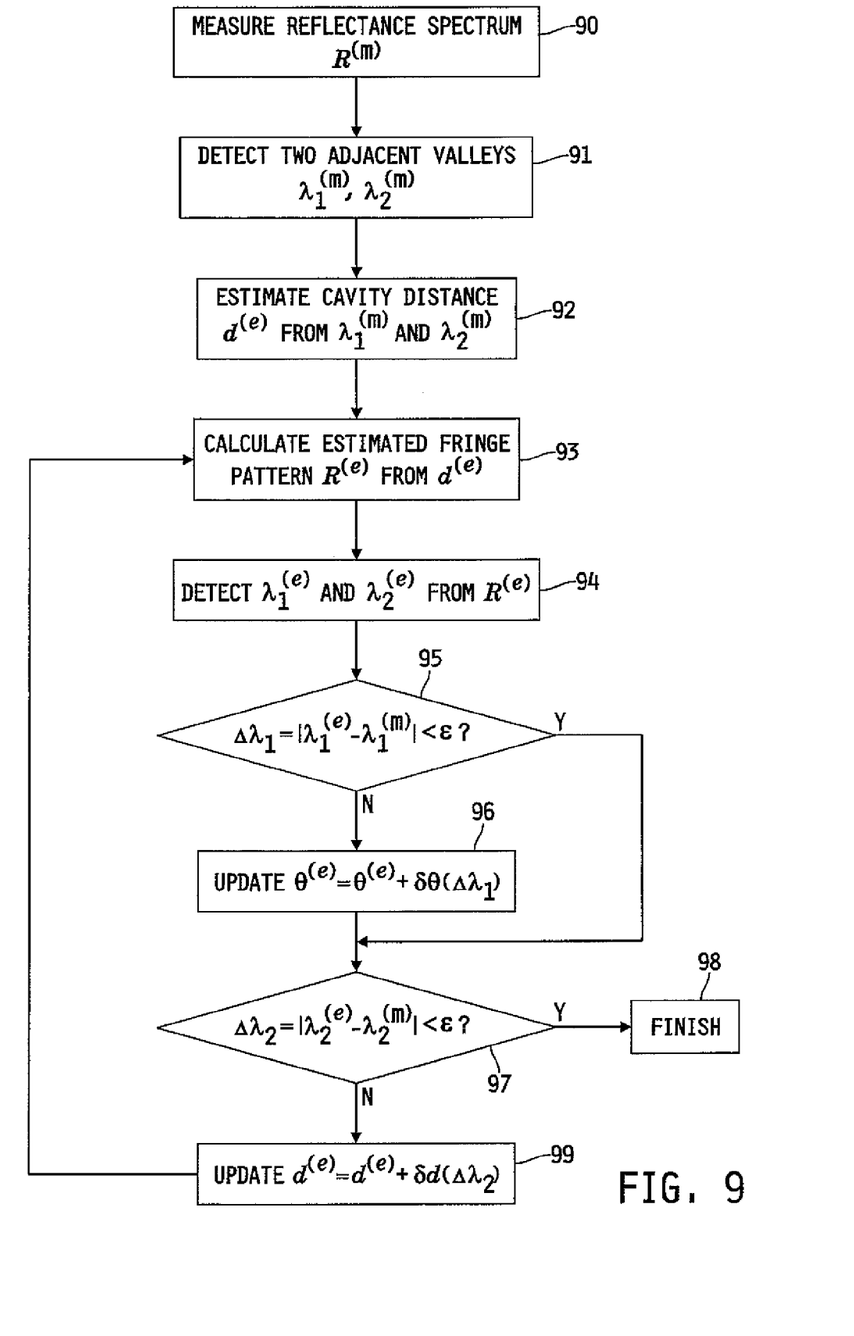
FIG. 9 is a flowchart of the steps performed by the system and method of the present invention for two fringe matching.

Step One: Two-Fringe Match for Rough Estimation of the Distance and the Phase Shift A flow chart illustrating the steps of the fringe-matching algorithm is illustrated in FIG. 9. First, the reflectance spectrum $R^{(m)}$ is measured as illustrated at block 90. Then, the wavelengths of two adjacent fringes, $\lambda_1^{(m)}$ and $\lambda_2^{(m)}$, are detected from the measured fringe spectrum $R^{(m)}$ as illustrated at block 91 and the first estimation of the cavity distance $d^{(e)}$ is calculated from Equation (3) as illustrated at block 92. Next, the estimated distance $d^{(e)}$ and a randomly selected phase shift $\theta^{(e)}$ are plugged into Equation (2) to calculate the estimated fringe spectrum $R^{(e)}$ as illustrated at block 93. Two adjacent fringes, $\lambda_1^{(e)}$ and $\lambda_2^{(e)}$, in $R^{(e)}$ are detected in the vicinity of the two measured fringes, $\lambda_1^{(m)}$ and $\lambda_2^{(m)}$ as illustrated at block 94. If $\Delta\lambda_1 = |\lambda_1^{(e)} - \lambda_1^{(m)}|$ is larger than a pre-determined threshold $\epsilon$ as illustrated at block 95, then a correctional phase shift $\delta\theta(\Delta\lambda_1)$ is calculated as:

Equation (4):

$$\delta\theta = -4\pi n_m d^{(e)} \left( \frac{1}{\lambda_1^{(m)}} - \frac{1}{\lambda_1^{(e)}} \right).$$

The estimated phase shift $\theta^{(e)}$ can thus be updated as illustrated at block 96 as:

Equation (5):

$$\theta^{(e)} = \theta^{(e)} + \delta\theta = \theta^{(e)} - 4\pi n_m d^{(e)} \left( \frac{1}{\lambda_1^{(m)}} - \frac{1}{\lambda_1^{(e)}} \right).$$

The fringe spectrum is updated from the newly estimated phase shift $\theta^{(e)}$ and two adjacent fringes, $\lambda_1^{(e)}$ and $\lambda_2^{(e)}$, in the vicinity of $\lambda_1^{(m)}$ and $\lambda_2^{(m)}$ are found. Since Equation (5) essentially provides that $\lambda_1^{(e)} = \lambda_1^{(m)}$, a correctional distance $\delta d$ is calculated from the difference between $\lambda_2^{(e)}$ and $\lambda_2^{(m)}$:

Equation (6):

$$\delta d = -\frac{\lambda_1^{(e)}}{2(\lambda_2^{(e)} - \lambda_1^{(e)})} \left( \frac{\lambda_2^{(e)}}{\lambda_2^{(e)} - \lambda_1^{(e)}} - 1 \right) (\lambda_2^{(e)} - \lambda_2^{(m)})$$

A new estimated distance is calculated from this correctional distance as illustrated at block 99 as:

$$d^{(e)} = d^{(e)} + \delta d_1 \qquad \text{Equation (b 7):}$$

Figure 10:
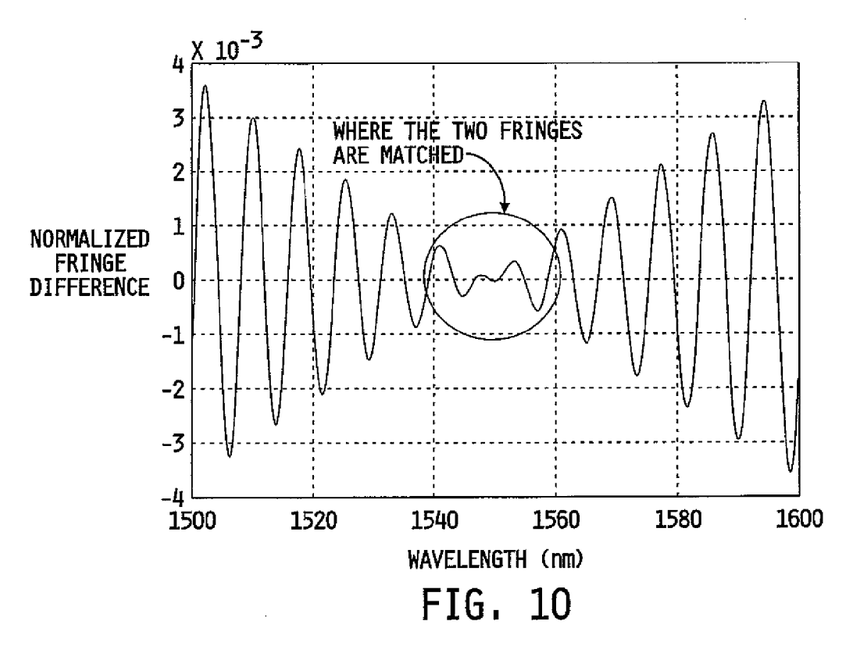
FIG. 10 is a graph illustrating the normalized difference between estimated and measured fringe spectrum.

The estimated fringe spectrum $R^{(e)}$ is then calculated from the updated $d^{(e)}$ and the next iteration starts. The iteration continues until $\Delta\lambda_1$ and $\Delta\lambda_2$ are smaller than $\epsilon$ as illustrated at blocks 97 and 98, indicating the measured and the estimated fringe spectra agree with each other at the two wavelengths $\lambda_1^{(m)}$ and $\lambda_2^{(m)}$. However, matching these two fringes does not guarantee that the estimated distance and phase shift are the same as $d_0$ and $\theta_0$ because the difference between the estimated and measured fringe spectrum can be small around the two matched fringes but is pretty large at other wavelengths as shown in FIG. 10. The estimated distance and phase shift $d^{(e)}$ and $\theta^{(e)}$ need to be further refined using the information extracted from the fringe difference.

Figure 11:
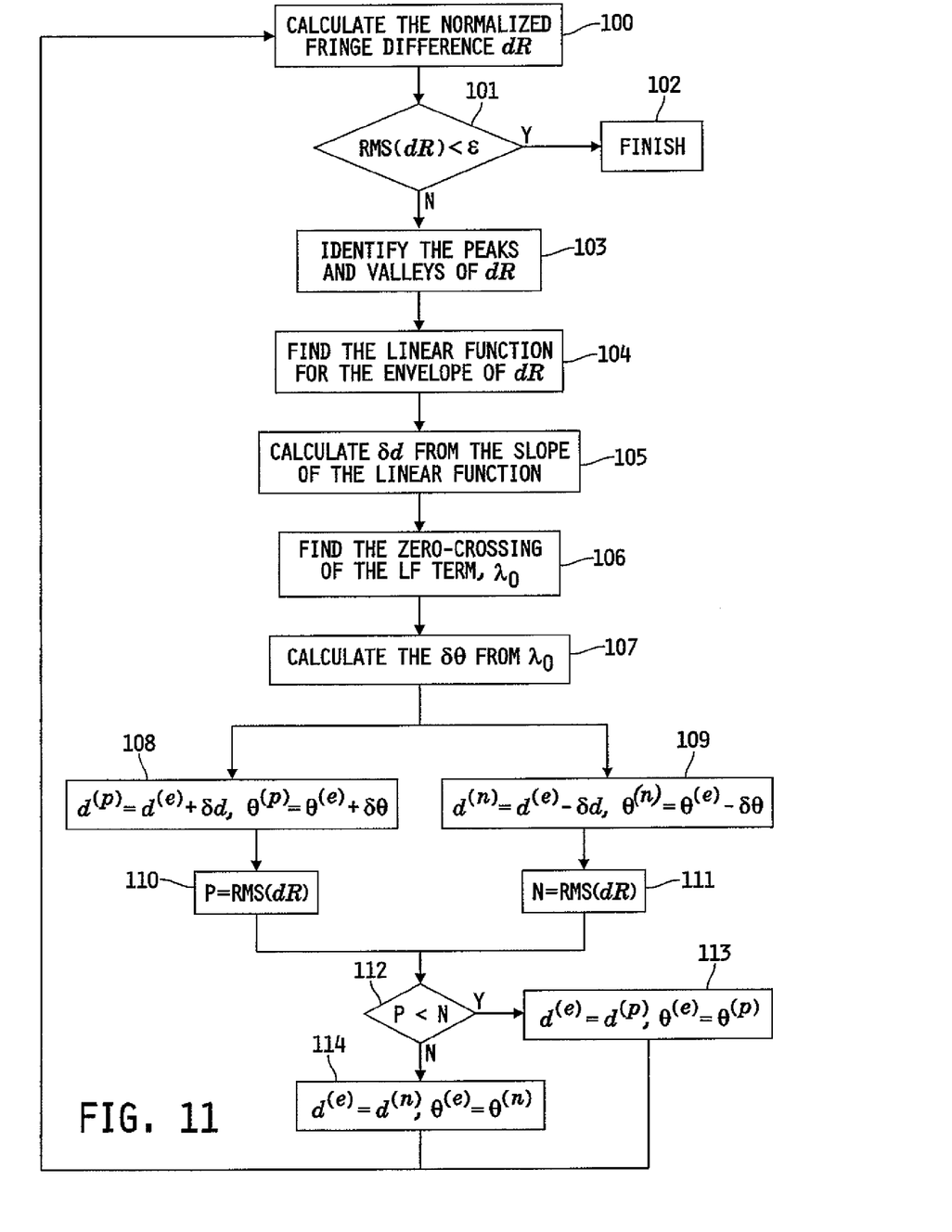
FIG. 11 is a flowchart illustrating the steps performed during the precise estimation of the distance and phase shift from the normalized fringe difference.

Step Two: Precise Estimation of the Distance and the Phase Shift From the Normalized Fringe Difference A flow chart illustrating the steps for estimating the distance and the phase from the normalized fringe difference is shown in FIG. 11. The normalized fringe difference is first calculated as illustrated at block 100. Next, if the root-mean-square of the fringe difference is smaller than a pre-determined threshold, $\epsilon$, as illustrated at block 101, the algorithm is finished as illustrated at block 102. The normalized fringe difference is calculated at block 100 as:

Equation (8):

$$d\bar{R} = \frac{R^{(e)} - R^{(m)}}{4T_{co}(\lambda)T_{clad}(\lambda)} = \sin\left[ \frac{2\pi\Delta n L_{cav}}{\lambda} + \frac{(\theta_0 + \theta^{(e)})}{2} + \frac{\pi(d_o + d^{(e)})}{\lambda} \right]$$

$$\sin\left[ \frac{2\pi(d_o - d^{(e)})}{\lambda} + \frac{(\theta_0 - \theta^{(e)})}{2} \right],$$

which contains two terms; a higher frequency (HF) term $$\sin\left[ \frac{2\pi\Delta n L_{cav}}{\lambda} + \frac{(\theta_0 + \theta^{(e)})}{2} + \frac{\pi(d_o + d^{(e)})}{\lambda} \right]$$

and the lower frequency (LF) term $$\sin\left[ \frac{2\pi(d_o - d^{(e)})}{\lambda} + \frac{(\theta_0 - \theta^{(e)})}{2} \right].$$

The HF term contributes to the periodic behavior of the fringe difference while the LF term modulates the amplitude of the HF term. The LF term can be also considered as the envelope of the fringe difference. Because $d_0 - d^{(e)}$ and $\theta^0 - \theta^{(e)}$ are relative small when the two fringes are matched, the LF term is approximately a linear function of $1/\lambda$, as follows:

Equation (9):

$$\sin\left[ \frac{2\pi(d_o - d^{(e)})}{\lambda} + \frac{(\theta_0 - \theta^{(e)})}{2} \right] \approx 2\pi(d_o - d^{(e)})\frac{1}{\lambda} + \frac{(\theta_0 - \theta^{(e)})}{2} =$$

$$2\pi\delta d \frac{1}{\lambda} + \frac{\delta\theta}{2}.$$

Figure 12:
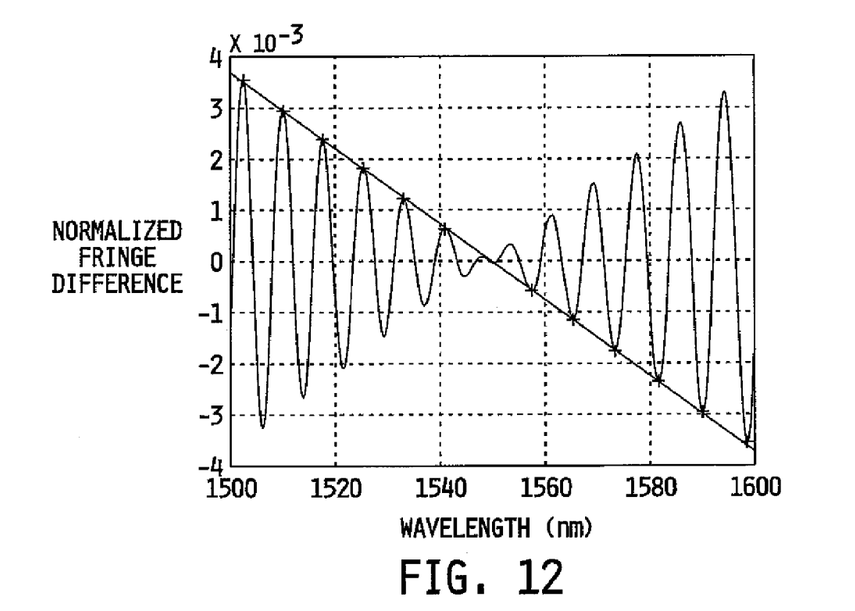
FIG. 12 is a graph illustrating a linear fitting of the envelope of the normalized fringe difference.

Therefore, we can calculate the correctional terms $\delta d$ and $\delta\theta$ if the envelope of the normalized fringe difference is known. The linear function of the envelope is obtained by finding the peaks and valleys of the fringe difference as illustrated at block 103 and then linear fit the peaks and the valleys as illustrated at block 104. A graph illustrating a linear fitting of the envelope of the normalized fringe difference is shown in FIG. 12.

Expressing the linear function as:

$$f(1/\lambda) = A(1/\lambda) + B, \qquad \text{Equation (10)}$$

the correctional distance $\delta d$ is calculated from the slope of the fitting function A as:

Equation (11):

$$\delta d = \frac{A}{2\pi}.$$

The correction phase shift $\delta\theta$ is calculated from the zero-crossing of the linear function as illustrated at block 106. If the zero-crossing of the linear function does not fall into the spectrum window, the location of the zero-crossing is calculated from Equation (12) as follows:

Equation (12):

$$\lambda_0 = -\frac{A}{B}.$$

Figure 13:
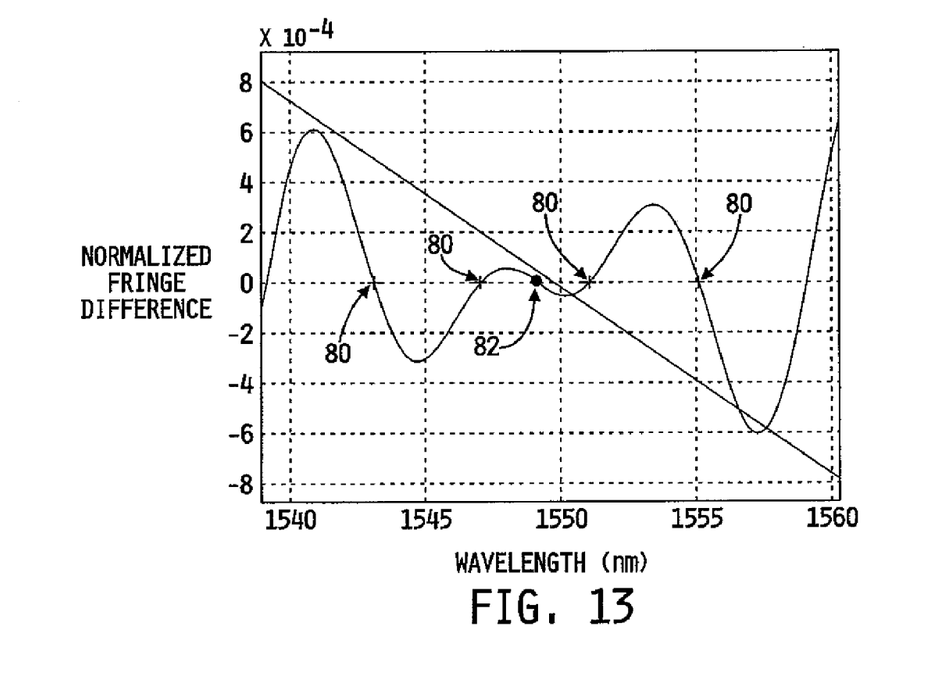
FIG. 13 is a graph illustrating the precise identification of the zero crossings from the fringe difference.

However, the precise location of zero-crossing can be identified from the zero-crossing of the fringe difference if the fit line intersects the x-axis at a point within the spectrum window. As shown in FIG. 13, the zero-crossings of the fringe difference as identified by the crosses 80 are the zero-crossings contributed by the HF terms while the zero-crossing identified by the center circle 82 is the zero-crossing of the LF term. The zero-crossing of the fitting function is not coincident with the zero-crossing of the fringe difference due to fitting errors. As a result, using the zero-crossing of the fringe difference as identified by the circle 82 for the calculation is more accurate than using the zero-crossing of the fitting line. At the zero-crossing $\lambda_0$ of the LF term, is as follows:

Equation (13):

$$\sin\left[\frac{2\pi(d_o - d^{(e)})}{\lambda_0} + \frac{(\theta_0 - \theta^{(e)})}{2}\right] = 0 \Rightarrow \delta\theta = -\frac{4\pi\delta d}{\lambda_0} = -\frac{2A}{\lambda_0}.$$

Figure 14A:
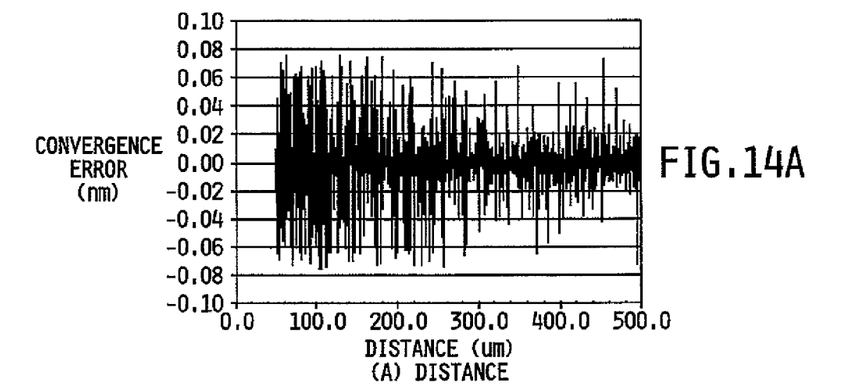
FIGS. 14A and 14B are graphs illustrating convergence errors for distances from 50 μm to 500 μm.
Figure 14B:
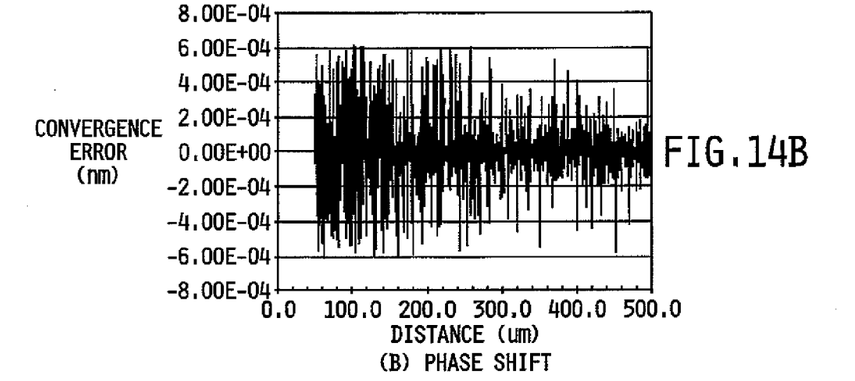

Depending on whether the peaks or the valleys of the fringe difference are selected, the slope of the fitting curve can be either positive or negative in FIG. 12. Therefore, the correction of the distance and phase shift are calculated for both cases, i.e., $d^{(p)}=d^{(e)}+\delta d, \theta^{(p)}=\theta^{(e)}+\delta\theta$; and $d^{(n)}=d^{(e)}-\delta d, \theta^{(n)}=\theta^{(e)}-\delta\theta$ as illustrated at blocks 107, 108, and 109. The root-mean-square of the fringe difference for both cases are calculated and compared as illustrated at blocks 110, 111, and 112. The case that results in a smaller root-mean-square is chosen for the next iteration as illustrated at blocks 113 and 114. The iteration continues until the root-mean-square of the fringe difference is smaller than a pre-determined threshold, $\epsilon$ as illustrated at block 101 and 102. In the illustrated embodiment, the algorithm converges to the correct distance and the phase shift with ultra-high accuracy for a large dynamic range, as shown in FIGS. 14A and 14B. The data interrogation algorithm described above is applicable to Fabry-Perot interferometry as well.

Application of the Sensing Systems

In addition to distance/displacement measurement, this invention can be applied for near-field surface profiling, vibration measurement, temperature measurement, pressure measurement, refractive index measurement, and bio/chemical detection.

Near-Field Surface Profiling

One of the applications of the sensing system is for near-field surface profiling. Currently, optical near-field surface profiling is mainly accomplished by a Near-field Scanning Optical Microscopy (NSOM). NSOM overcomes the diffraction limit of conventional optical microscopes by positioning a tapered optical fiber probe in the near-field of the sample, and has hence become a widely used technique for the optical investigation of materials in the sub-wavelength range. However, the technique's further advancement, especially in the field of biology and surface chemistry, is hindered due to its position feedback mechanism. Moreover, despite a variety of light collecting techniques in NSOM, the basic image construction technique has relied on the direct detection of the sample light using a photomultiplier tube. Therefore, it has the same drawbacks as the intensity-based sensors.

The illustrated distance sensor is capable of measuring ultra-small distances down to the nanometer range. Unlike the conventional NSOMs that require a complicated position feedback mechanism to position the probe, the application of the present distance sensor for near-field surface profiling does not require any additional position feedback mechanism because the absolute distance between the sensor probe and the sample surface is readily available. Furthermore, the distance measurement is based on WLI and thus is much more robust and more sensitive than the direct detection of the sample light. Application of the LPFG-based distance sensor for near-field surface profiling enables the development of a more economical, more robust, and more powerful NSOM. The present sensor may also resolve the difficulties associated with imaging live cells and surface chemistry using existing NSOMs.

The LPFG-based distance sensor has an OPD includes two distance components, the distance L between the LPFG and the fiber end, and the cavity distance d, as shown in Equation (1). This gives it exceptional flexibility with respect to the minimum distance it can measure. To measure a smaller cavity distance, the distance L is increased to maintain the same number of fringes in the spectral window. As a result, the LPFG-based optical fiber distance sensor can measure ultra-small cavity distances down to the nanometer range. This characteristic may be applied for near-field surface profiling.

Figure 15:
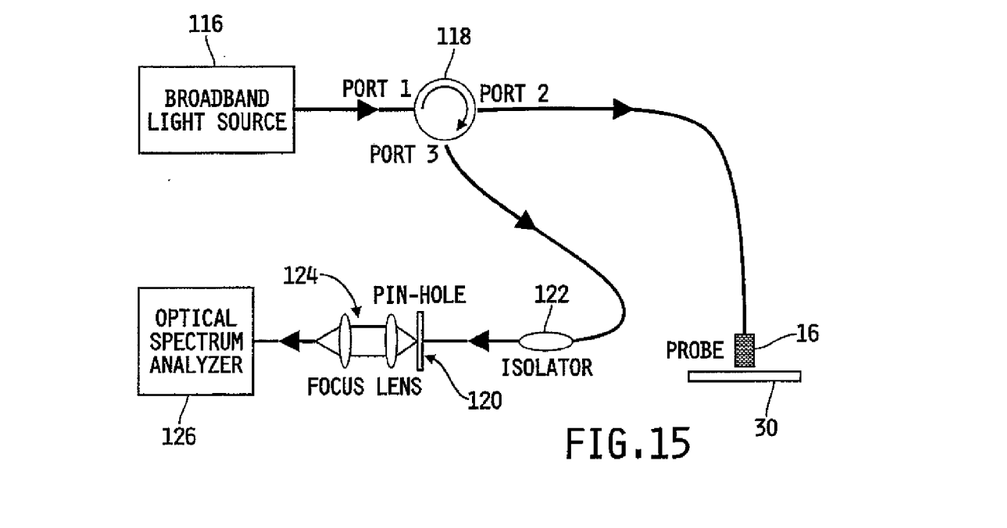
FIG. 15 is a diagrammatical view illustrating near-field surface profiling using the LPFG-based distance sensor of the present invention.

Unlike the far-field surface profiling that has a resolution limited by the optical diffraction limit, the near-field surface profiling does not have an inherent resolution limit. Therefore, it is widely used for the characterization of nanoscale structures. Because the illustrated distance sensor can measure absolute distance down to the nanometer range, it can serve as a non-contact near-field profilometer. The application of the LPFG-based distance sensor for near-field surface profiling is shown in FIG. 15. Whitelight from a broadband light source 116 is coupled to port 1 of an optical circulator 118. Port 2 of optical circulator 118 is coupled to probe 16, and port 3 of optical circulator 118 is coupled to an optical isolator 122. The sensor probe 16 is illustratively positioned in the near field of the sample 30, at about 50–100 nm away from the sample surface. The output spectrum is routed toward a pin-hole 120 after passing the optical isolator 122. The light that passes through the pin hole 120 is collected by the focus lenses 124 and is coupled to the OSA 126. Distance between the probe 16 and the sample surface 30 is then extracted from the measured fringe spectrum. The resolution of the system is determined by the size of the pin hole 120. Because the cavity distance is measured directly, no sophisticated position feedback mechanism is required to ensure proper positioning of the sensor probe 16. In addition, the WLI distance measurement has ultra-high precision and is insensitive to unwanted fluctuation in signal intensity.

Simultaneous Temperature and Distance Measurement

Equations (2) and (3) indicate that the cavity distance d is determined by the spectral positions of any two adjacent fringes while the fringe envelope is related to the length, the period, and the coupling coefficient of the LPFG. As the temperature changes, it alters the grating period of the LPFG due to thermal expansion, resulting in a shift of the fringe envelope. Therefore, the temperature can be measured by detecting the central wavelength of the fringe envelope. It is expected that the illustrated LPFG-based distance sensor has a linear relationship between the surrounding temperature and the envelope shift. Not only does the sensor's capability to measure temperature and distance simultaneously enhance its functionality, it also improves its distance measurement accuracy since compensation techniques can be applied to correct the measured distance based on the temperature measurement.

Intensity-Based Fringe Pattern Interpretation

Figure 16:
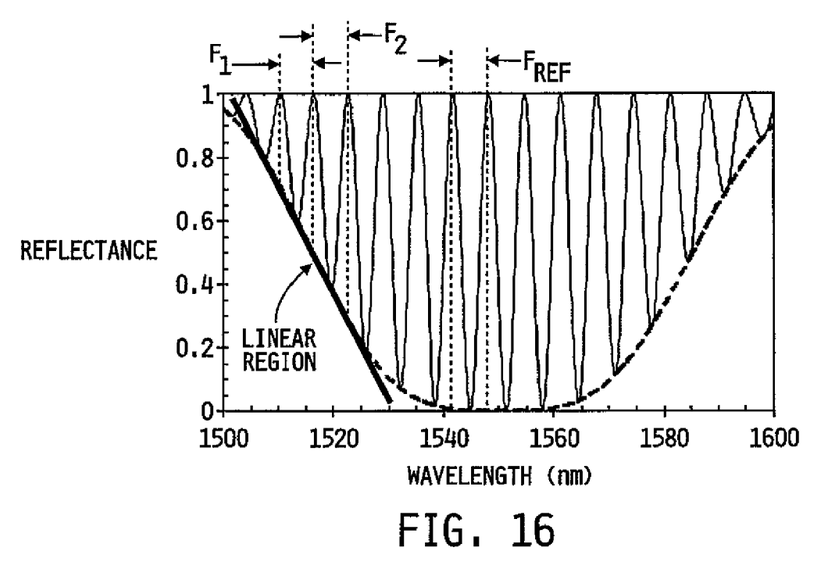
FIG. 16 is a graph illustrating filtering of the reflectance spectrum for intensity-based data interrogation.
Figure 17:
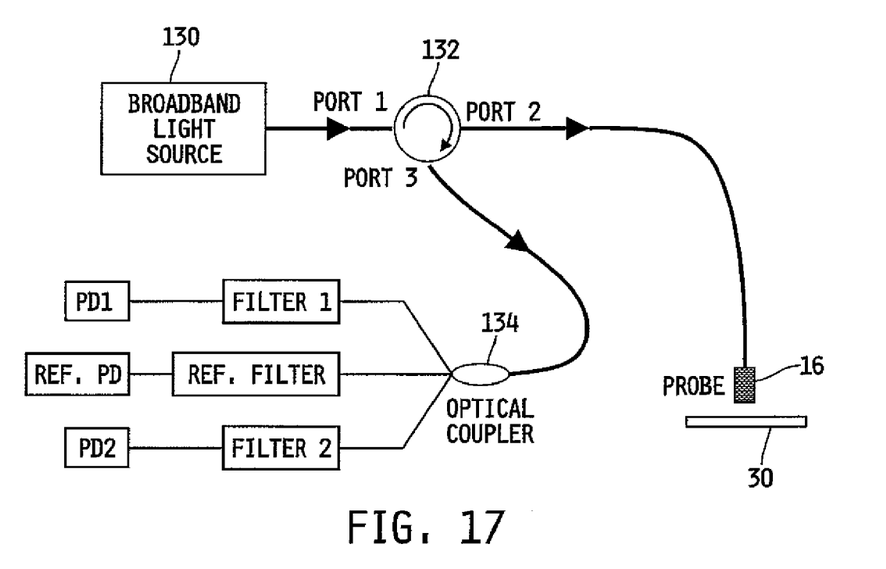
FIG. 17 is a diagrammatical view illustrating an intensity-based data processing system.

As shown in FIG. 16, the fringe spectrum is modulated by the LPFG transmittance and part of the fringe envelope is nearly linear. If a band-pass optical filter is used to filter out one fringe from the fringe spectrum in this linear region, the intensity of the filtered signal is directly proportional to its fringe position. Therefore, the LPFG transmittance acts as a wavelength-to-intensity converter and the fringe position can be determined from the output intensity of the filtered signal. Since only the positions of two adjacent fringes are needed to calculate the absolute cavity distance, two optical filters, $F_1$ and $F_2$, may be used as depicted in FIG. 16, to filter out two adjacent fringes. The positions of these two fringes are then measured from the intensities of the filtered signals from $F_1$ and $F_2$. Therefore, an intensity-based data interrogation technique may be used to overcome the slow sampling rate of the spectrum scanning device such as an OSA. A diagram of the intensity-based data interrogation system is shown in FIG. 17. Whitelight from a broadband light source 130 is coupled to port 1 of an optical circulator 132. Port 2 of optical circulator 132 is coupled to probe 16, and port 3 of optical circulator 132 is coupled to an optical coupler 134. The output optical wave passes through optical coupler 134 and is separated into three waves and these waves are filtered by three band-pass optical filters. The intensities of the output signals from Filter 1 and Filter 2 are measured by the photo diodes PD 1 and PD 2, respectively. In order to compensate for the unwanted intensity changes due to laser power fluctuations and fiber bending losses etc., a reference filter is introduced to provide a reference signal. The reference filter is positioned at the center of the fringe spectrum where the spectrum envelope has a relatively flat region. The intensity measurements of the filtered signals from $F_1$ and $F_2$ are acquired into a computer and normalized with the intensity of the reference signal. The fringe positions are then derived from the normalized intensities. Finally, the absolute distance is calculated from the fringe positions. This self-calibrated intensity-based data interrogation scheme has as fast a sampling rate and rapid transient response as an intensity-modulated sensor, while preserving the ultra-high sensitivity and large dynamic range of a WLI sensor.

Acoustic Emission Detection

Acoustic emission (AE) signal is generally defined as the release of elastic energy in a material under load, and it appears as a transient stress wave. It is widely adopted to evaluate the damage of mechanical structures. AE signals are small-amplitude broadband ultrasonic waves, mainly in the 100 KHz to 1 MHz range. Therefore, an AE detector should have an ultra-high sensitivity and a fast transient response. Optical fiber sensors have been in development for the detection of AE signals, mostly based on either Mach-Zehnder or Fabry-Perot interferometers (FPI). However, these interferometric AE sensors usually require electronic phase demodulation systems and thus add weight and power consumptions to the system. The intensity-based data interrogation technique described above can be applied to implement a low cost and power efficient system for AE detection. Since it is only necessary to monitor the detected power using inexpensive photodiodes, the processing overhead can be greatly reduced as compared to competing systems.

Figure 18:
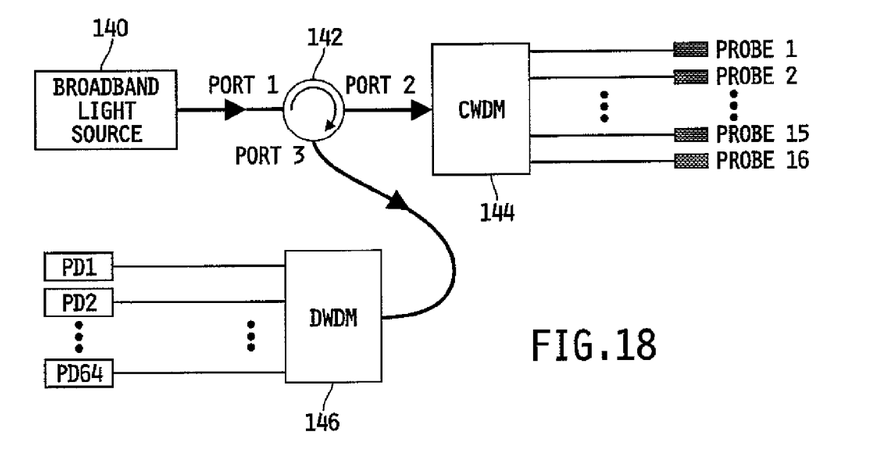
FIG. 18 is a diagrammatical view illustrating the use of CWDM and DWDM for sensor multiplexing.

The illustrated whitelight FPI sensor may be designed so that commercially available passive Coarse Wave Division Multiplexing (CWDM) and Dense Wave Division Multiplexing (DWDM) components can be used for sensor multiplexing and data interrogation. As shown in FIG. 18 whitelight from a broadband light source 140 is coupled to port 1 of an optical circulator 142. Port 2 of optical circulator 132 is coupled to a CWDM 144, and port 3 of optical circulator 142 is coupled to a DWDM 146. CWDM 144 is used to separate the incoming whitelight into 16 channels and direct them to sixteen (16) FPI probes. At the output end, DWDM 146 is used so that each channel of the DWDM 146 serves as one band-pass filter and the output intensities of these DWDM channels are directly related to the fringe positions, from which the disturbances of the cavity length can be detected.

Pressure and Refractive Index Measurement

Figure 3:
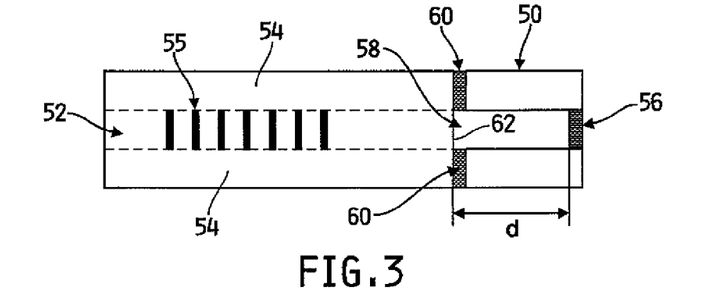
FIG. 3 is a diagram of an another embodiment of an optical fiber pressure sensor.

Another application of the illustrated in-fiber whitelight interferometric sensor is pressure measurement sensor. As shown in FIG. 3, a tube 50 includes an inner core 52 and an outer cladding 54. An LPFG 55 is located in core 52. A reflective membrane 56 covering the end of the tube 50 can be bound to the fiber. The tube 50 can be sealed so that a free space 58 formed between the membrane 56 and the fiber end 62 is a vacuum or it has a hole so that pressure can be applied into the free space 58. A mirror 60 covers the cladding 55. As pressure is applied to the membrane 56, either from inside or from outside, the membrane 56 will deflect, resulting in a distance change between the fiber end 62 and the membrane 56. The applied pressure can be then deducted from the deflection of membrane, which is measured by the change of the distance (d) using the techniques discussed herein.

The optical fiber sensor depicted in FIG. 3 can be also used for refractive index measurement. If there is an opening in the tube 50, the medium of the free space 56 between the membrane 56 and the fiber end 62 will be the same as the surrounding environment. With the geometries of the LPFG 55, the cavity length, and the distance (d) between the fiber end and the membrane 56 known, the refractive index of the medium can be calculated from the reflectance spectrum. In addition, any variations that could change the refractive index of the medium, being it temperature, chemical deposition, or biological agent, will cause a shift of the reflectance spectrum and thus can be detected. Consequently, this optical fiber sensor can be applied for liquid level measurement, chemical composition measurement, and/or bio-agent detection.

Mechanical Testing of MEMS Thin Films

Figure 19:
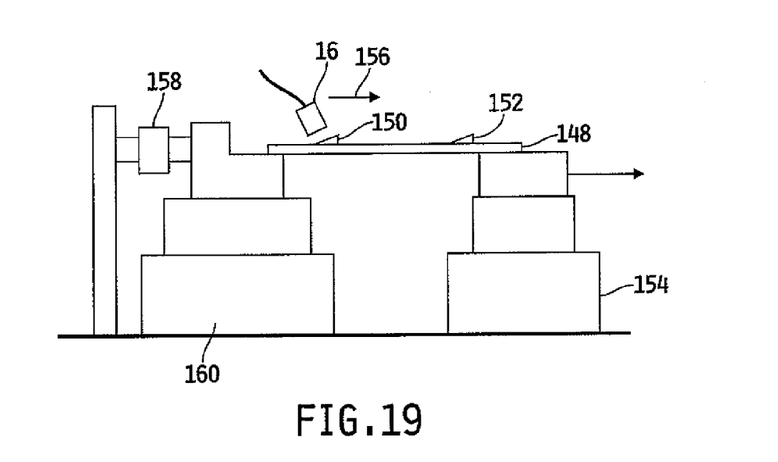
FIG. 19 is a schematic illustration of a micro-testing system.

The application of the sensing system for mechanical testing of thin films is shown in FIG. 19. The sample under testing is illustratively a thin film 148 with two gage markers 150, 152 that have an angled surface relative to the thin film surface 148. The optical fiber sensor 16 is mounted on a nano-translation stage 154 with the end surface perpendicular to the surface of the gage markers 150, 152. At the beginning of the test, the sensor probe 16 is scanned from one gage marker 150 to the other 152 to determine the lateral distance between these two gauge markers 150, 152. As the thin film 148 stretches under tension, the gage markers 150, 152 move away from their original positions. The distance between the sensor head 16 and the marker surface will change accordingly. Scanning the sensor probe 16 along the gage area again in the direction of arrow 158 determines the new distance between these two gage markers 150, 152 under a specific tensile load, from which a stress-strain curve can be constructed for material property interpretation. FIG. 19 illustrates a load cell 158 and a frictionless station 160 used in the testing.

Although the invention has been described in detail with reference to certain preferred embodiments, variations and modifications exist within the scope and spirit of the present invention as described and defined in the following claims.

What is claimed is:

1. A sensing method using an optical fiber sensor, the method comprising:
   providing a probe including an optical fiber having an inner core region, an outer cladding region, and a long period fiber grating (LPFG) embedded at selected distances from a distal end of the optical fiber;
   forming a reflective surface over the cladding region at the distal end of the optical fiber;
   positioning the distal end of the optical fiber adjacent a sample;
   supplying light to the core of the optical fiber so that upon encountering the LPFG, a first portion of the light wave travels through the core of the optical fiber toward a distal end and a second portion of the light wave is coupled into the cladding region and travels through the cladding region toward distal end;
   emitting the first portion of the light wave moving through core from the distal end of the optical fiber, the first portion of the light wave striking a surface of the sample and being reflected back into the core, the sample reflective wave moving through the core in a direction away from the distal end;
   reflecting the second portion of the light wave off the reflective surface so that a cladding reflective wave moves back through the cladding region in a direction away from the distal end, a portion of the cladding reflective wave being coupled back to core at the LPFG; and
   determining a distance between the distal end of the optical fiber and the surface of the sample based on a phase shift between the cladding reflective wave and the sample reflective wave.

2. The method of claim 1, wherein the probe is formed by:
   depositing a negative photoresist layer on the distal end of the optical fiber;
   coupling a UV light source to an end of the optical fiber opposite of the distal end to expose a portion of the photoresist layer covering the core;
   creating a photomask on the core by removing the photoresist layer from the cladding;
   depositing a metallic layer on the distal end of the optical fiber over the cladding region and over the photomask on the core region; and
   removing the photomask from the core region to expose the core region while leaving the metallic layer on the cladding region.

3. The method of claim 2, wherein the metallic layer is one of a gold and an aluminum metallic film.

4. The method of claim 1, wherein the determining step comprises:
   obtaining an estimate of the distance between the distal end of the optical fiber and the sample surface and the phase shift by matching two fringes in an estimated fringe spectrum with two fringes in a measurement fringe spectrum; and
   calculating the distance between the distal end of the optical fiber and the sample surface and the phase shift more precisely from the difference between the measured fringe spectrum and the estimated fringe spectrum.

5. The method of claim 1, further comprising correcting the distance measured in the determining step based a temperature measurement.

6. The method of claim 1, further comprising the step of using the probe to measure displacement of the sample with nanometer resolution.

7. The method of claim 1, further comprising the step of using the probe to measure temperature.

8. The method of claim 1, wherein the determining step comprises:
   filtering a fringe spectrum to obtain filtered signals from two adjacent fringes;
   measuring the positions of the two filtered fringes using intensities of the filtered signals; and
   calculating the distance between the distal end of the optical fiber and the surface of the sample based on the measured positions of the two filtered fringes.

9. The method of claim 1, wherein the sample is a thin film material.

10. The method of claim 1, wherein the sensor is used as a near-field scanning optical microscope.

11. The method of claim 1, wherein the sensor is used as an acoustical emission detector.

12. The method of claim 1, wherein the sample is a membrane spaced apart from the distal end of the optical fiber to define a free space therebetween, the method further comprising the measuring pressure applied to the membrane based on a change in the distance between the membrane and the distal end of the optical fiber.

13. The method of claim 1, wherein the sample is a membrane spaced apart from the distal end of the optical fiber to define a free space therebetween, the method further comprising providing an opening in communication with the free space, and calculating a refractive index in the free space to detect at least one of liquid level measurement, chemical composition measurement, and bio-agent detection based upon changes in the calculated refractive index.

14. An optical fiber sensor comprising:
   a probe including an optical fiber having an inner core region, an outer cladding region, a long period fiber grating (LPFG) embedded at selected distances from a distal end of the optical fiber, and a reflective surface located over the cladding region at the distal end of the optical fiber;
   a light source coupled to the optical fiber, the light source supplying light to the core of the optical fiber so that, upon encountering the LPFG, a first portion of the light wave travels through the core region in a direction toward a distal end and a second portion of the light wave is coupled into the cladding region and travels through the cladding region in a direction toward distal end, the first portion of the wave being emitted from core at the distal end of the optical fiber, the first portion of the light wave striking a surface of a sample and being reflected back into the core, the sample reflective wave moving back through the core region in a direction away from the distal end, and the second portion of the light wave being reflected by the reflective surface to form a cladding reflective wave that moves back through the cladding region in a direction away from the distal end, a portion of the cladding reflective wave being coupled back to core at the LPFG; and an analyzer optically coupled to the probe to determine a distance between the distal end of the optical fiber and the surface of the sample based on a phase shift between the cladding reflective wave and the sample reflective wave.

15. The sensor of claim 14, further comprising an optical circulator having a first port coupled to the light source, a second port coupled to the probe, and a third port coupled to the analyzer.

16. The sensor of claim 14, further comprising an optical coupler coupled between the third port of the optical circulator and the analyzer.

17. The sensor of claim 14, wherein the light source is a broadband light source.

18. The sensor of claim 14, further comprising:
an optical circulator having a first port coupled to the light source, a second port coupled to the probe, and a third port;
an optical isolator coupled to the third port of the optical circulator;
a pin-hole located adjacent the optical isolator; and
a focusing lens located adjacent the pin hole collect light from the pin hole, the focusing lens being coupled to the analyzer.

19. The sensor of claim 14, further comprising:
an optical circulator having a first port coupled to the light source, a second port coupled to the probe, and a third port;
an optical coupler coupled to the third port of the optical circulator;
first and second band pass optical filters coupled to the optical coupler, the first and second band pass optical filters filtering out two adjacent fringes from a fringe spectrum; and
first and second intensity detectors coupled to the first and second band pass optical filters, respectively, the distance from the distal end of the optical fiber and the surface of the sample being calculated based on the detected intensities of the two adjacent fringes.

20. The sensor of claim 19, further comprising a reference filter coupled to the optical coupler to provide a reference signal, the reference filter being used to calibrate the intensities detected by the first and second intensity detectors.

21. The sensor of claim 20, wherein the reference filter is positioned at a center of a fringe spectrum where the spectrum envelope has a relatively flat region.

22. The sensor of claim 19, wherein the first and second intensity detectors are photo diodes.

23. The sensor of claim 14, further comprising a optical circulator having a first port coupled to the light source, a second port coupled to a coarse wave division multiplexing component configured to separate the incoming light into a plurality of channels, a separate probe being coupled to each of the plurality of channels, a third port of the optical circulator being coupled to dense wave division multiplexing component having a plurality of output channels, and an intensity detector coupled to each output channel of the division multiplexing component.

24. The sensor of claim 14, wherein the distance from the distal end of the optical fiber and the surface of the sample is calculated with nanometer resolution.

25. The sensor of claim 14, wherein the sample is a membrane spaced apart from the distal end of the optical fiber to define a free space therebetween, and further comprising means for measuring pressure applied to the membrane based on a change in the distance between the membrane and the distal end of the optical fiber.

26. The sensor of claim 14, wherein the sample is a membrane spaced apart from the distal end of the optical fiber to define a free space therebetween with an opening in communication with the free space, and further comprising means for calculating a refractive index in the free space to detect at least one of liquid level measurement, chemical composition measurement, and bio-agent detection based upon changes in the calculated refractive index.

27. The sensor of claim 14, wherein the analyzer is an optical spectrum analyzer.

* * * * *